(12) United States Patent  
Pariseau

(10) Patent No.: US 9,140,639 B2  
(45) Date of Patent: Sep. 22, 2015

(54) PULSE SCOPE FOR PARTICLE COUNTER

(71) Applicant: Particles Plus, Inc., Canton, MA (US)

(72) Inventor: David Pariseau, Los Altos, CA (US)

(73) Assignee: Particles Plus, Inc., Stoughton, MA (US)

(*) Notice: Subject to any disclaimer, the term of this patent is extended or adjusted under 35 U.S.C. 154(b) by 0 days.

(21) Appl. No.: 14/214,895

(22) Filed: Mar. 15, 2014

(65) Prior Publication Data

US 2014/0268141 A1 Sep. 18, 2014

Related U.S. Application Data

(60) Provisional application No. 61/786,658, filed on Mar. 15, 2013.

(51) Int. Cl.
*G01N 15/02* (2006.01)
*G01N 15/14* (2006.01)

(52) U.S. Cl.
CPC ........ *G01N 15/1429* (2013.01); *G01N 15/0205* (2013.01); *G01N 15/1459* (2013.01); *G01N 2015/0238* (2013.01); *G01N 2015/1486* (2013.01)

(58) Field of Classification Search
CPC .......... G01N 15/0205; G01N 15/0211; G01N 15/1459; G01N 2021/4716; G01N 15/1434
USPC .......................................... 356/336
See application file for complete search history.

(56) References Cited

U.S. PATENT DOCUMENTS

| 3,696,399 | A | * | 10/1972 | Klein et al. | .......... | 341/139 |
| 3,919,050 | A | * | 11/1975 | Curby | .......... | 435/39 |
| 6,137,572 | A | * | 10/2000 | DeFreez et al. | .......... | 356/336 |

* cited by examiner

*Primary Examiner* — Tarifur Chowdhury
*Assistant Examiner* — MD Rahman

(57) ABSTRACT

An airborne, gas, or liquid particle sensor with an on-board data acquisition system that can be used to capture detailed particle pulse information. The information can be used both for on-board analysis and reporting as well as off-line analysis and reporting.

11 Claims, 6 Drawing Sheets

PULSE SCOPE FOR PARTICLE COUNTER

CROSS-REFERENCE TO RELATED APPLICATION

This application claims priority to U.S. Provisional Application Ser. No. 61/786,658 filed on Mar. 15, 2013, titled PULSE SCOPE FOR PARTICLE COUNTER by inventor David Pariseau, the entire disclosure of which is hereby incorporated herein by reference.

This application is related to and incorporates by reference U.S. Non-Provisional application Ser. No. 14/214,899, filed herewith on Mar. 15, 2014, titled PARTICLE COUNTER WITH INTEGRATED BOOTLOADER by inventor David Pariseau; U.S. Non-Provisional application Ser. No. 14/214,870, filed herewith on Mar. 15, 2014, titled PERSONAL AIR QUALITY MONITORING SYSTEM by inventors David Pariseau and Adam Giandomenico; U.S. Non-Provisional application Ser. No. 14/214,903, filed herewith on Mar. 15, 2014, titled MIXED-MODE PHOTO-AMPLIFIER FOR PARTICLE COUNTER by inventors David Pariseau and Ivan Horban; U.S. Non-Provisional application Ser. No. 14/214,876, filed herewith on Mar. 15, 2014, titled MULTIPLE PARTICLE SENSORS IN A PARTICLE COUNTER by inventor David Pariseau; U.S. Non-Provisional application Ser. No. 14/214,889, filed herewith on Mar. 15, 2014, titled INTELLIGENT MODULES IN A PARTICLE COUNTER by inventor David Pariseau; and U.S. Non-Provisional application Ser. No. 14/214,907, filed herewith on Mar. 15, 2014, titled PULSE DISCRIMINATOR FOR PARTICLE COUNTER by inventors David Pariseau and Ivan Horban.

BACKGROUND OF THE INVENTION

Particle counters have been used for decades in manufacturing or industrial applications to measure particulate quantities in air, gases or liquids. Typically such counters would also bin particulates by size. These size bins vary by application and often by instrument. A particle counter has at least one size channel and popular counters can have 6 or more channels. Typically these size channels discriminate pulses based on the pulse height of the incoming signal. The pulse height refers to the peak voltage of the signal. Sometimes there is also rudimentary discrimination of pulse width, often in hardware. These systems provide a go/no-go qualification for an incoming pulse, typically they are implemented in hardware and provide a simple gate function such that pulses below a minimum duration are excluded from counting. The intent is to reject noise, typically at the most sensitive resolution where the signal-to-noise ratio is the poorest. However, conventional particle counters simply count a number of particles in the atmosphere. Therefore, what is needed is a system and method to have a particle counter that provides more information about particles in the atmosphere than just a particle count.

SUMMARY

In accordance with the various aspects of the present invention, a system and method are provided that are capable or providing more information about particles in the atmosphere than just a particle count. The foregoing is a summary and thus includes, by necessity, simplifications, generalizations and omissions of detail. Those skilled in the art will appreciate that the summary is illustrative only and is not intended to be in any way limiting

BRIEF DESCRIPTION OF THE DRAWINGS

The foregoing summary as well as the following detailed description is better understood when read in conjunction with the appended drawings. For the purpose of illustrating the invention, there is shown in the drawings exemplary constructions of the invention; however, the invention is not limited to the specific various aspects, embodiments, methods and instrumentalities disclosed in the drawings.

DETAILED DESCRIPTION

Figure 1:
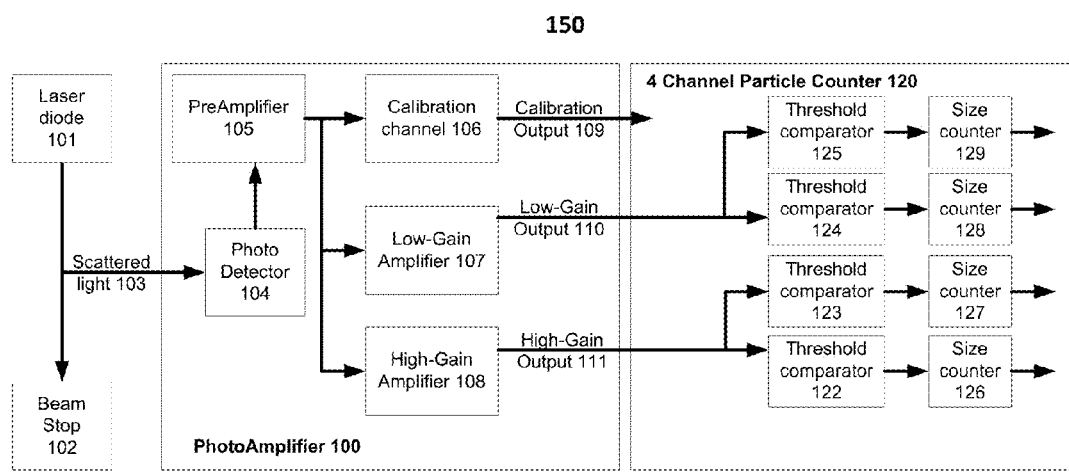
FIG. 1 shows a system in accordance with the various aspects of the present invention.

It is noted that, as used in this description, the singular forms "a," "an" and "the" include plural referents unless the context clearly dictates otherwise. Reference throughout this specification to "one aspect," "another aspect," "at least one aspect," "various aspects," "further aspect," "one embodiment," "an embodiment," "certain embodiments," or similar language means that a particular aspect, feature, structure, or characteristic described in connection with the embodiment or embodiments is included in at least one aspect or embodiment of the present invention. Thus, appearances of the phrases "in accordance with one aspect," "in accordance with various aspects," "in accordance another aspect," "one embodiment," "in at least one embodiment," "in an embodiment," "in certain embodiments," and similar language throughout this specification may, but do not necessarily, all refer to the same embodiment.

In accordance with the various aspects of the present invention, a device includes a computing device. As referred to herein, the devices may be part of a system or the system. It may be implemented to include a central processing unit (e.g., a processor), memory, input devices (e.g., keyboard and pointing devices), output devices (e.g., display devices), and storage device (e.g., disk drives). The memory and storage device are computer-readable media that may contain instructions or code that, when executed by the processor or the central processing unit, cause the device to perform certain tasks. In addition, data structures and message structures may be stored or transmitted via a data transmission medium, such as a signal on a communications link. Various communications channels may be used (e.g., the Internet, a local area network (LAN), a wide area network (WAN), or a point-to-point dial-up connection, or any other wireless channel or protocol) to create a link.

In accordance with the various aspects of the present invention, the device or system may be use various computing systems or devices including personal computers, server computers, hand-held or laptop devices, multiprocessor systems, microprocessor based systems, programmable consumer electronics, network personal computers (PCs), minicomputers, mainframe computers, distributed computing environments that include any of the above systems or devices, and the like. In accordance with the various aspects of the present invention, the device or system may also provide its services to various computing systems such as personal computers, cell phones, personal digital assistants, consumer electronics, home automation devices, and so on.

In accordance with the various aspects of the present invention, the device or system may be described in the general context of computer-executable instructions, such as program modules or code, which is executed by one or more computers or devices. Generally, program modules include routines, programs, objects, components, data structures, and so on that perform particular tasks or implement particular data types. Typically, the functionality of the program modules may be combined or distributed as desired in various embodiments.

Where a range of values is provided, it is understood that each intervening value, to the tenth of the unit of the lower limit unless the context clearly dictates otherwise, between the upper and lower limit of that range and any other stated or intervening value in that stated range, is encompassed within the aspects of the present invention. The upper and lower limits of these smaller ranges may independently be included in the smaller ranges and are also encompassed within the aspects of the present invention, subject to any specifically excluded limit in the stated range. Where the stated range includes one or both of the limits, ranges excluding either or both of those included limits are also included in the aspects of the present invention.

Referring now to FIG. 1, in accordance with aspects and embodiments of the present invention, an example of a four-channel particle counter front-end 150 is shown below. In this example a beam present between the laser diode (101) and the beam stop (102) scatters light (103) as particles cross that beam. Typically the scattered light (103) is focused by reflectors onto the face of a photo-diode (104) on a photo-amplifier board (100). The tiny current in the photo-diode is then pre-amplified, usually by a trans-impedance amplifier (105). The pre-amplified signal is usually available on a calibration channel (106) for use during calibration. The pre-amplifier (105) signal is also sent to one or more amplifiers. In this case there are two, a low-gain channel (107) and a high-gain channel (108). These amplifiers further increase the signal amplitude and transmit send it, often, to a separate particle counting board (120). On this board the incoming pulse signals are sorted into size bins. In this example there are four channels, two channels (122,123) connected to the high-gain amplifier (111) and two channels (124,125) connected to the low-gain amplifier (110). The threshold comparators (122,123,124, 125) are setup during the calibration phase so that they each channel counts pulses above some threshold. This can be a manual process with manual adjustment of a potentiometer, or a programmatic process where firmware would set a digital potentiometer or digital-to-analog converter. The counter outputs (126,127,128,129) would then be read by microcontroller and displayed to the user. Typically, no data is collected on each pulse. Its occurrence is simply recorded as a count in the appropriate size bin.

A similar system functions for gases other than air, and liquids. It also functions for counters that use a light-blocking rather than a light-scattering architecture, except that pulses in light-blocking systems see a decrease in light as the particles pass through the beam.

Figure 2:
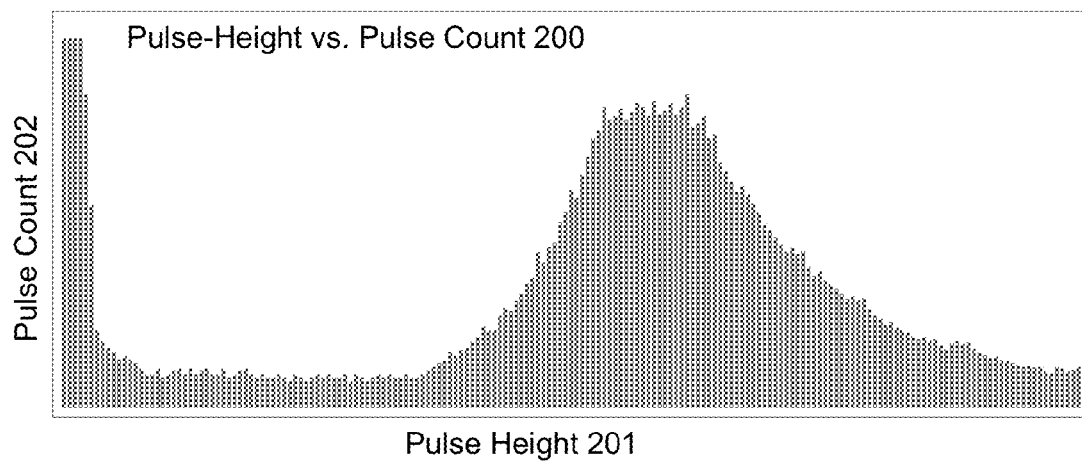
FIG. 2 shows a graph of an output for an analyzer in accordance with the various aspects of the present invention.

For the purposes of calibration, a pulse-height analyzer (PHA) or multi-channel analyzer (MCA) is typically used to capture the peak-heights of incoming pulses while calibrated particulates of a known size are introduced into the system. An example of an output from such an analyzer is shown in FIG. 2.

The incoming peak pulse-heights (201) (typically in millivolts) are captured with each size capture being added to a separate size bin counter. The number of counts for each bin (202) is used to form a histogram of pulse-heights vs. pulse-counts (200). This type of plot is used to determine the threshold value to setup for a channel in order to detect particles of a minimum size. It is also used to ensure adequate separation between channels and above the noise floor.

In some embodiments, particle counters, also referred to as "particle counter systems," include circuitry to capture a peak-pulse heights on the particle counter itself. Here, the counter passes this information to a calibration system that makes all the calculations. In another example, this analysis is done by an external analyzer, which gets connected to the particle counter during calibration.

In certain embodiments, in addition to capturing the occurrence of pulses or aggregate count of particles above some calibrated threshold, the particle counter provides the means of logging more information about each pulse and capturing information on individual pulses.

In certain embodiments, the particle counter records one or more of the following information on individual pulses as they arrive at the front-end: time of arrival; peak pulse height; pulse width; and individual samples within the pulse to define the pulse envelope.

None of this data is currently stored by any existing particle counter on a pulse-by-pulse basis. Typically this data is only collected or used in aggregate (based on bin size), and in those situations none of the individual data is retained for use or analysis.

Capturing this data makes possible analyses and reports that have been previously unavailable in particle counting instruments. This data can be used both locally by the instrument to provide views, graphs, or charts either to the display or to a local printer. It can also be sent to an external device or computer for post-analysis or reporting. More options are thus available for post-analysis since all the source data is present for analysis, not just aggregated data.

Figure 3:
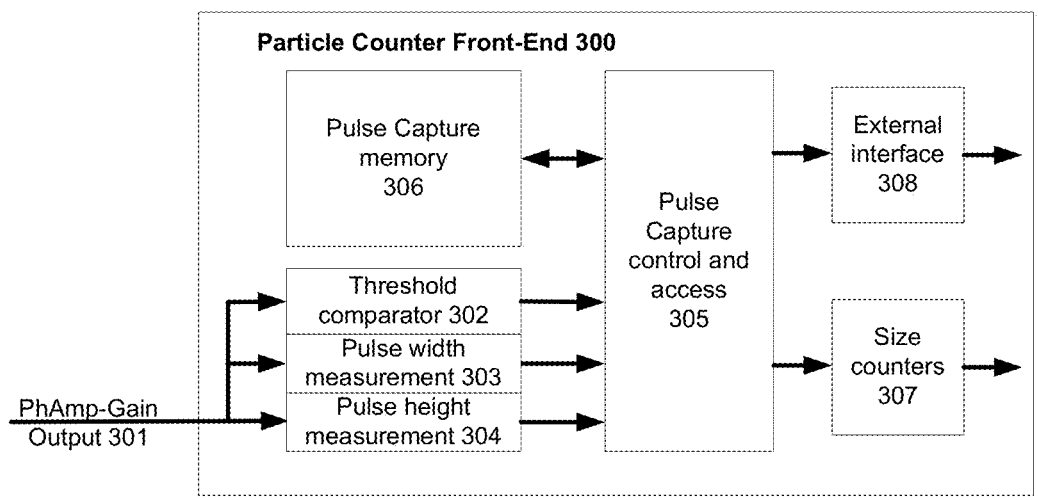
FIG. 3 shows a system in accordance with the various aspects of the present invention.

Referring now to FIG. 3, in certain aspects and embodiments, data is captured on a pulse by pulse basis. A particle counter includes a photo-amplifier (such as photo-amplifier 100 above), a threshold comparator (302) coupled to the photo-amplifier, a pulse width measurement device (303) coupled to the photo-amplifier, and a pulse height measurement device (304) coupled to the photo-amplifier, each of which is coupled to pulse feature capturing and control circuitry (305) that collects parametric information on pulses generated by the photo-amplifier. The Particle Counter Front-End (300), is comprised of one or more pulse threshold comparators (302).

For each pulse qualified above threshold, the Pulse Capture and Control circuitry (305) collects parametric information, which is implemented via programmable logic (like an FPGA, or CPLD) or via dedicated hardware (like an ASIC, or discrete logic components), for example. This control logic would direct specialized hardware to collect parametric information on the pulse. As noted, parameters might include time-of-arrival which can be done by an on-chip counter, or pulse width (303), which might also be possible using the same on-chip counter and the time a pulse spends above threshold. The pulse peak height (304) is typically accomplished using a peak detector, which is read once the pulse has passed (falls below threshold), and then reset.

It's also possible given this level of control over the incoming pulse stream to setup a large number of counters or bins, since detailed parametrics are available for each pulse. So, an on-board, or off-board PHA or MCA could easily be created based on this information. The captured pulse data could be stored in a local memory (306), and available to other devices in a system via an external interface (308). Since such an implementation can generate a significant amount of data (compared to previous aggregate-only systems), some implementations might only store data in certain situations, when a trigger event was present for example. Examples of triggers that would force the system to log individual pulse data include: a button trigger, either hard or soft button to enable/disable logging; counts for a specified channel above some predefined threshold; external device request, via external communications link; and a log of pulses that meet a certain defined profile (e.g. with minimum and maximum pulse width).0

Alternatively or in combination, the particle counter continuously logs data in a circular buffer where historic data is made available, the depth of this being history a function of the memory size and the incoming pulse rate.

Once parametric pulse data has been captured, it makes a number of analyses and reports possible.

Figure 4:
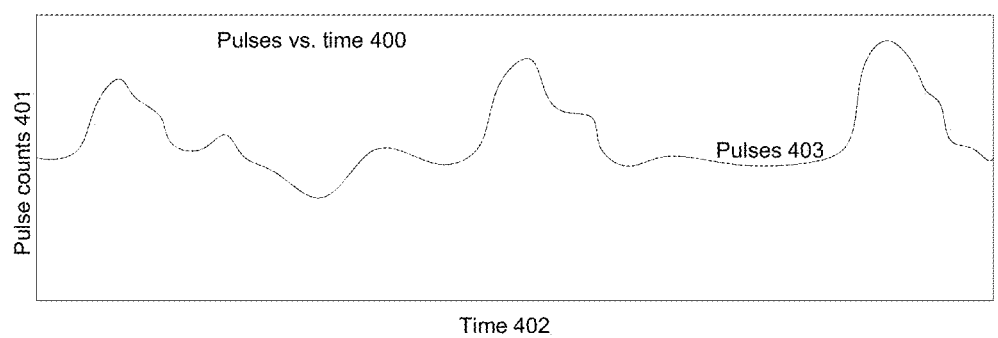
FIG. 4 shows a graph of pulse counts in accordance with the various aspects of the present invention.

Referring now to FIG. 4, one possible view/report for this collected data is to provide a particle counts vs. time, shows an example of a line graph showing Pulse counts over time (400). In certain embodiments, report 400 provides data associated with a resolution of pulse logging rate, which is limited by the channel sizes.

In certain embodiments, the pulse counts for a captured dataset is calculated after the sample is collected for some arbitrary threshold. For example, the pulse size threshold could be defined after the fact, and used to filter the captured data to calculated the counts above that threshold over the time and displayed as shown above with the calculate pulses (403) tracing a line over time (402). Similarly, the same can be done with multiple traces also definable by the user, other possible number of traces are also contemplated.

There are some products out there that plot counts over time, but these act only on aggregated data and can only deal with macro events that are typically measured in seconds. By having access to the actual counts themselves we can see much finer detail than is currently possible. With events in the millisecond or microsecond range, or perhaps even into the nanosecond range.

Referring to report 400, it appears that the pulse counts for the defined waveform are periodic with maxima occurring on three separate peaks, reasonably evenly spaced. This type of graph is useful for correlating particulate events with external phenomena, for example, machine or process cycle times. If the time scale was defined in milliseconds it can correlate to some mechanical processes for example a failed bearing on a motor spewing small bursts of particles at a rapid rate that a normal particle counter (reporting only in aggregate data) would be unable to discern.

Figure 5:
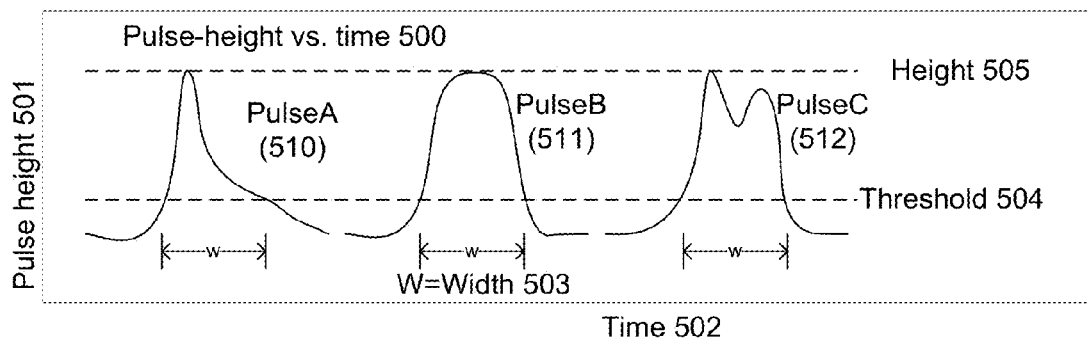
FIG. 5 shows a graph of pulse-height vs time in accordance with the various aspects of the present invention.

Referring to FIG. 5, in certain embodiments, three separate pulses are shown (510,511,512) all of which have the same threshold (504), the same pulse-width (503) above that threshold, and the same peak pulse-height (505). Here, the three pulses (510,511,512) are quite different. PulseA (510) is very narrow and fast, though the width is the same as the others. PulseB (511) is broad and has a reasonably flat peak. PulseC (512) appears to be the two separate pulses (possibly the result of nearly coincident particles passing through the detector).

Conventional particle counting hardware and firmware doesn't make any distinction between these three pulses, not considering width at all, so pulses with widths shorter and longer than these, but with the same peak pulse-height would all be treated similarly in contemporary particle counters.

Figure 6:
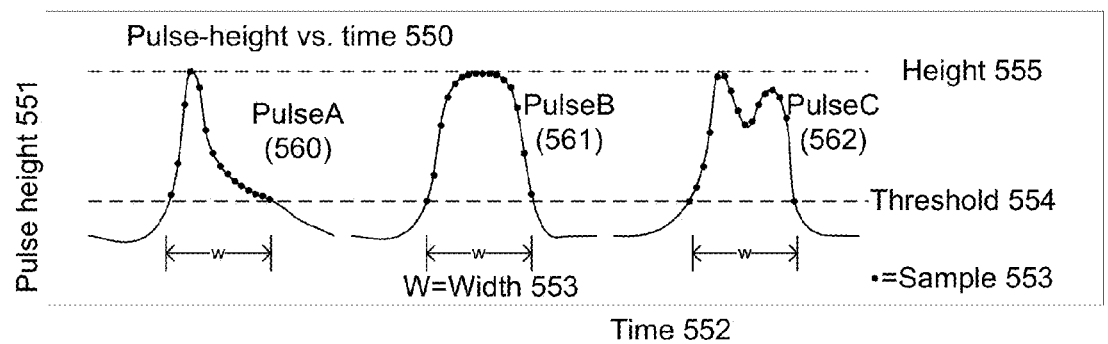
FIG. 6 shows a graph of pulse-height vs time in accordance with the various aspects of the present invention.

Referring now to FIG. 5 and FIG. 6, by taking multiple samples for each pulse while it is above threshold (504), the differences between the pulses are discernible. In the example below, the same pulses are sampled multiple times, while above threshold (554). These samples are stored for display or analysis. The samples are indicated by dots (553) and the number of samples was chosen to simplify the drawing. In certain embodiments, the sample rate is fixed or at a configurable sample rate. Here, the samples are used to reconstruct the pulse shapes with an acceptable level of precision. Increasing the sample rate, increases the precision.

Storing pulse information for some pulses, or for all pulses that meet some trigger event, or in some cases all pulses all the time, provides some additional capabilities to the particle counter system. In addition to being able to discriminate the above pulse shapes and perhaps treat these pulses differently in the particle counter. In certain embodiments, detailed pulse information allows the particle counter system to at least one of: measure repetitive noise imparted on the waveforms; filter out such repetitive noise from waveforms to yield increased signal-to-noise performance; and flag a sensor for service if the noise floor exceeds some fixed or configurable threshold.

As can be seen from the examples above, this detailed pulse data can make possible new analyses and ways of looking at data, manipulating it in order to arrive at a more complete understanding of particulate phenomena generating the incoming counts. This makes possible new techniques for isolating problems and discerning the source of contaminants in order to eliminate or contain them and speed resolution of such to increase manufacturing yields.

While various embodiments have been described above, it should be understood that they have been presented by way of example only, not limitation, and various changes in form and details may be made. Any portion of the device, instrument, apparatus and/or methods described herein may be combined in any combination, except mutually exclusive combinations. The aspects and embodiments described herein can include various combinations and/or sub-combinations of the functions, components and/or features of the different embodiments described. For example, multiple, distributed processing systems can be configured to operate in parallel.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

It will be apparent that various aspects of the present invention as related to certain embodiments may be implemented in software, hardware, application logic, or a combination of software, hardware, and application logic. The software, application logic and/or hardware may reside on a server, an electronic device, or be a service. If desired, part of the software, application logic and/or hardware may reside on an electronic device and part of the software, application logic and/or hardware may reside on a remote location, such as server.

In accordance with the aspects disclosed in the teachings of the present invention and certain embodiments, a program or code may be noted as running on a device, an instrument, a system, or a computing device, all of which are an article of manufacture. Additional examples of an article of manufacture include: a server, a mainframe computer, a mobile telephone, a multimedia-enabled smartphone, a tablet computer, a personal digital assistant, a personal computer, a laptop, or other special purpose computer each having one or more processors (e.g., a Central Processing Unit, a Graphical Processing Unit, or a microprocessor) that is configured to execute a computer readable program code (e.g., an algorithm, hardware, firmware, and/or software) to receive data, transmit data, store data, or perform tasks and methods. Furthermore, an article of manufacture (e.g., device) includes a non-transitory computer readable medium having a series of instructions, such as computer readable program steps or code, which is encoded therein. In certain aspects and embodiments, the non-transitory computer readable medium includes one or more data repositories, memory, and storage, including non-volatile memory. The non-transitory computer readable medium includes corresponding computer readable program or code and may include one or more data repositories. Processors access the computer readable program code encoded on the corresponding non-transitory computer readable mediums and execute one or more corresponding instructions. Other hardware and software components and structures are also contemplated.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, representative illustrative methods and materials are described herein.

All publications and patents cited in this specification are herein incorporated by reference as if each individual publication or patent were specifically and individually indicated to be incorporated by reference and are incorporated herein by reference to disclose and describe the methods and/or system in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A particle counter system comprising:
   at least one particle sensor including at least one photo-amplifier, the at least one photo-amplifier includes an output; and
   at least one peak-detector to determine a pulse height for the output of the at least one photo-amplifier; and
   at least one threshold comparator to count particles for pulse heights above at least one of a set threshold and a configurable threshold;
   at least one pulse data-logging channel that processes pulse height outputs of the at least one peak-detector,
   wherein the pulse data-logging channel is used to log, at least, pulse height outputs from the at least one peak-detector.

2. The particle counter system of claim 1, wherein data associated with the individual pulses is logged to a volatile memory.

3. The particle counter system of claim 1, where data associated with the individual pulses is logged to a non-volatile memory.

4. The particle counter system of claim 1, wherein the at least one threshold comparator used to determine a pulse width for pulses above a noise threshold, and wherein the pulse width is also logged by the data-logging channel recording the pulse height.

5. The particle counter system of claim 4, where individual pulses are filtered by a trigger event before being logged.

6. The particle counter system of claim 5, where the trigger event is pulse height.

7. The particle counter system of claim 5, where the trigger event is pulse width.

8. The particle counter system of claim 5, where the trigger event is a combination of pulse height and pulse width.

9. The particle counter system of claim 5, where the trigger event is an external signal.

10. The particle counter system of claim 5, where the trigger event is controlled by a different controller.

11. The particle counter system of claim 4, where the logged data is subsequently used to reconstruct a pulse stream over time.

* * * * *